United States Patent [19]

Bloom et al.

[11] 4,178,446

[45] Dec. 11, 1979

[54] SULFAM(NA)PHTHALEINS

[75] Inventors: Stanley M. Bloom, Waban; Alan L. Borror, Lexington; James W. Foley, Andover, all of Mass.

[73] Assignee: Polaroid Corporation, Cambridge, Mass.

[21] Appl. No.: 835,998

[22] Filed: Sep. 23, 1977

[51] Int. Cl.² .......................................... C07D 275/06
[52] U.S. Cl. ............................. 544/33; 260/239 R; 548/209; 544/62; 544/133; 544/135; 544/368; 546/95; 546/198
[58] Field of Search .............. 260/304 A, 293.57, 301; 544/33, 368, 133, 135, 62; 546/95

[56] References Cited

U.S. PATENT DOCUMENTS 3,702,244  11/1972  Bloom et al. ............................ 96/3

OTHER PUBLICATIONS

Dutt, S., J. Chem. Soc., 121, pp. 2389-2394 (1922).
Abramovitch, R., "J. Chem. Soc.", Perkin Translations 22, pp. 2589-2594 (1974).
Suzuki, H., "Electron Absorption Spectra and Geometry of Organic Molecules", 1967, pp. 114-116.
Breslow, R., "Organic Reaction Mechanisms", 1969.
Beilstein, "Handbuch der Organischen Chemie", vol. 27, p. 534.

Primary Examiner—Donald G. Daus
Assistant Examiner—Lisa Jones
Attorney, Agent, or Firm—Sybil A. Campbell

[57] ABSTRACT

This invention relates to phenol sulfam(na)phthaleins possessing a

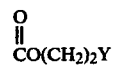

group wherein Y represents an electron-withdrawing group substituted on the N atom of the sulfam(na)phthalein ring, which compounds find utility as photographic optical filter agents and filter agent precursors.

40 Claims, 2 Drawing Figures

SULFAM(NA)PHTHALEINS

BACKGROUND OF THE INVENTION

1. Field of the Invention

The present invention relates to novel chemical compounds and, more specifically, it relates to novel sulfam(na)phthaleins useful as optical filter agents and filter agent precursors in photographic processes for protecting an exposed photosensitive material from post-exposure fogging during development in the presence of ambient light.

2. Description of the Prior Art

A number of diffusion transfer processes for producing photographic images in both black-and-white and in color have been proposed. Of particular interest are diffusion transfer processes wherein the image-receiving layer carrying the transfer image is not separated from the developed photosensitive layer(s) after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer. Diffusion transfer processes for forming images viewable without separation of the photosensitive and image-receiving components and integral negative-positive film units useful in such processes, i.e., film units wherein the negative or the photosensitive component and the positive or image-receiving component are retained as a permanent laminate after processing are described in U.S. Pat. Nos. 3,415,644, 3,415,645 and 3,415,646 issued Dec. 10, 1968 to Edwin H. Land, U.S. Pat. Nos. 3,573,043 and 3,573,044 issued Mar. 30, 1971 to Edwin H. Land and U.S. Pat. Nos. 3,594,164 and 3,594,165 issued July 20, 1971 to Howard G. Rogers.

U.S. Pat. No. 3,647,437 issued Mar. 7, 1972 to Edwin H. Land also is concerned with diffusion transfer processes wherein the resulting photograph comprises the developed photosensitive layer(s) retained with the image-receiving layer as part of a permanent laminate. In the processes disclosed in this patent, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. Though the pH-sensitive dye is usually included in the processing composition, it may be initially positioned in the film unit, for example, in a layer over the photosensitive element provided it is in its colorless form if photoexposure is to be effected through that layer. Upon application of an alkaline processing composition, the pH-sensitive dye is converted to its colored form, and after the desired processing time, it is converted back to its colorless form by reducing the environmental pH, e.g., by including an acid-reacting layer as part of the film unit. Examples of pH-sensitive dyes found particularly useful as optical filter agents are the phthalein and naphthalein dyes disclosed in U.S. Pat. No. 3,702,244 issued Nov. 7, 1972 to Stanley M. Bloom, Alan L. Borror, Paul S. Huyffer and Paul T. MacGregor and in U.S. Pat. No. 3,702,245 issued Nov. 7, 1972 to Myron S. Simon and David P. Waller and also the 9-pyridyl fluorene dyes disclosed in U.S. Pat. No. 3,726,675 issued Apr. 10, 1973 to Alan L. Borror.

Copending U.S. patent application Ser. No. 836,006, now U.S. Pat. No. 4,139,381 of Stanley M. Bloom, Alan L. Borror and James W. Foley filed concurrently herewith is concerned with the use of a different class of optical filter agents in integral negative-positive film units which are generated from substantially colorless filter agent precursor compounds and are capable of being discharged independently of a change in pH. The colorless filter agent precursor is initially disposed in a layer of the film unit, for example, in a layer coated over the photosensitive element, and subsequent to imagewise exposure of the photosensitive element, the colored optical filter agent is generated by contacting the colorless precursor with base, e.g., an aqueous alkaline processing composition. After remaining in contact with said base for a given time, the colored optical filter agent is discharged by forming a new compound which is substantially colorless and which is different from and non-reversible by a pH change to either said optical filter agent or said precursor. Compounds, i.e., optical filter agent precursors found useful for generating a colored optical filter agent above a given alkaline pH which, in turn, generates a colorless product above said given pH are those possessing (i) an ionizable proton removed in base to generate a chromophore and (ii) a moiety that undergoes an irreversible cleavage reaction with base with resultant destruction of said chromophore to yield a substantially colorless product.

Dutt, J. Chem. Soc., 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali. Also, it has been found that the compound corresponding to the structure given could not be synthesized by repeating the procedures reported by Dutt.

The present invention is directed to novel sulfam(na)phthaleins which find utility in the above-described photographic products and processes as colorless precursors for providing colored optical filter agents for protecting an imagewise exposed photosensitive element from further undesired exposure during processing in ambient light.

SUMMARY OF THE INVENTION

It is therefore the primary object of the present invention to provide novel sulfam(na)phthaleins.

It is a further object of the present invention to provide novel sulfam(na)phthaleins useful as optical filter agents and filter agent precursors in photographic processes conducted in ambient light and in photographic products useful in such processes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

According to the present invention, novel 3,3-disubstituted sulfam(na)phthaleins are provided which possess certain substituents on the N atom, i.e., in the 2-position of the sulfam(na)phthalein ring. The 3,3 substituents may be the same or different, and at least one of the 3,3 substituents is a color-producing moiety, i.e., a moiety possessing an ionizable proton that is removed in base to generate a chromophore. These compounds will be defined with greater particularity hereinafter.

As noted above, the subject compounds are useful as optical filter agents and filter agent precursors in photography. In the presence of base above a given alkaline pH, the colorless optical filter agent precursor compounds of the present invention generate a colored optical filter agent which decolorizes by undergoing an irreversible cleavage reaction with said base at a pH above said alkaline pH to yield a colorless product. Because of their ability to clear independently of a pH reduction, the subject filter agents and filter agent precursors may be employed in photographic processes where the pH of the system remains substantially unchanged subsequent to processing and also may be employed to permit early viewing of the final image in processes where the pH is reduced during the final stages of processing. Also, because the optical filter agent is irreversibly decolorized to a colorless product inert to changes in pH, the possibility of color reappearing in time due to accidentally increasing the pH is avoided.

For a fuller understanding of the nature and objects of the present invention, reference should be had to the following detailed description taken in connection with the accompanying drawings.

DETAILED DESCRIPTION OF THE INVENTION

Figure 1:
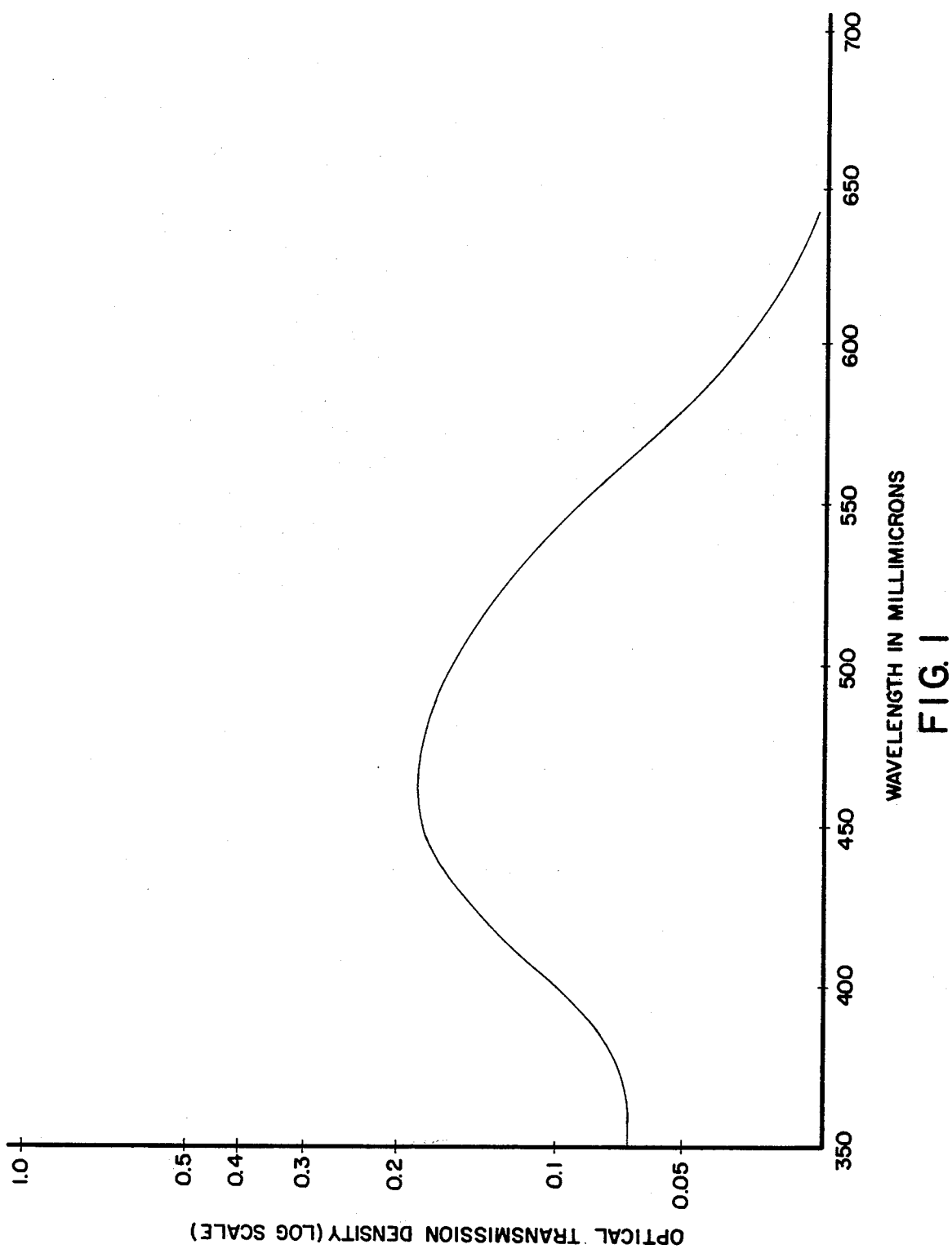
FIGS. 1 and 2 are graphic illustrations of the spectral absorption characteristics of the colored optical filter agents formed in basic solution by the colorless precursor compounds of the present invention represented hereinafter by the formulas designated (2) and (15). These graphs represent the optical transmission density, i.e., absorbance of the respective filter agents measured on a logarithm scale over the wavelength range of 350 nm to 700 nm.

According to the present invention, there are provided certain

2-$\overset{O}{\overset{\|}{C}}$O(CH$_2$)$_2$Y-3, 3-disubstituted sulfam(na)phthaleins wherein one of the 3,3 substituents is a 4'-hydroxyphenyl or a 4'-hydroxynaphthyl moiety and Y represents an electron-withdrawing group. These compounds in the presence of base above a given alkaline pH are converted from a colorless to a colored compound by the removal of the ionizable proton from the functional —OH of the 4'-hydroxyphenyl (or 4'-hydroxynaphthyl) moiety which is accompanied by the opening of the sulfam(na)phthalein ring. The colored compound formed in the presence of base is converted to a new compound, which is colorless, by irreversible cleavage of the 2-substituent of the sulfam(na)phthalein ring after remaining in contact with said base above a given alkaline pH, usually pH 10, for a predetermined time. The new compound produced, which possesses a different substituent in the 2-position of the sulfam(na)phthalein ring, not only is different from the colored compound and from the colorless precursor but also is non-reversible to either the colored compound or the colorless precursor by changes in pH.

The compounds of the present invention useful in providing colored optical filter agents in the manner described above may be represented by the formula:

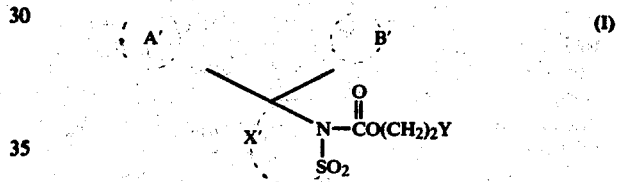

(1)

wherein A' is a 4'-hydroxyphenyl moiety or a 4'-hydroxynaphthyl moiety; B' is a phenyl moiety or a naphthyl moiety provided that A' is a 4'-hydroxyphenyl moiety when B' is a naphthyl moiety; X' represents the atoms necessary to complete a ring-closing moiety selected from a sulfamphthalein moiety and a sulfamnaphthalein moiety; and Y is an electron-withdrawing group. By "electron-withdrawing group" is meant a group having a positive sigma value as defined by Hammett's Equation.

By "sulfamphthalein" is intended a 2,3-dihydrobenz[d]isothiazole-1,1-dioxide moiety and by "sulfamnaphthalein" is intended a 2,3-dihydronaphtho[1,3-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

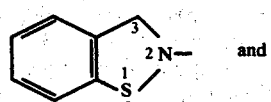

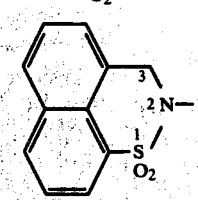

It will be understood that the A' moiety and/or the B' moiety and/or the ring-closing moiety of the compounds represented in formula I above may contain one or more substituents in addition to those specified, which substituents should not interfere with the intended use of the compounds.

In a preferred embodiment, the compounds of the present invention may be represented by the formula:

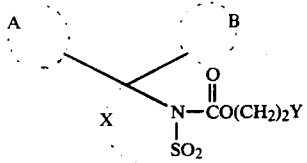
(II)

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete 2,3-dihydrobenz[d]isothiazole-1,1-dioxide or 2,3-dihydronaphtho[1,8-de]-1,2-thiazine-1,1-dioxide; and Y is an electron-withdrawing group having a sigma value greater than 0.60.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichlormethyl; sulfonamido (—NH—SO$_2$R$^o$ wherein R$^o$ is alkyl, aryl, alkaryl or aralkyl); sulfamoyl (—SO$_2$—NH—R$^o$ wherein R$^o$ has the same meaning given above); acyl

(—CR$^o$ wherein R$^o$ has the meaning given above); sulfonyl (—SO$_2$—R$^o$ wherein R$^o$ has the same meaning given above); sulfo; cyano; carboxy; hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine.

In a particularly preferred embodiment, the compounds of the present invention may be represented by the formula

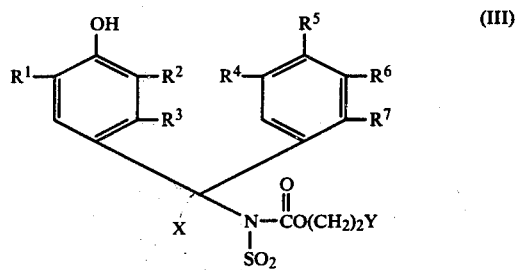
(III)

wherein R$^1$ and R$^2$ each are selected from hydrogen, alkyl, alkoxy, chloro and fluoro; R$^3$ is hydrogen, alkyl, alkoxy or hydroxy; R$^2$ and R$^3$ taken together represent the carbon atoms necessary to complete a fused benzene ring; R$^4$ and R$^6$ each are selected from hydrogen, alkyl, alkoxy, chloro and fluoro; R$^7$ is hydrogen, hydroxy, alkyl or alkoxy; R$^6$ and R$^7$ taken together represent the carbon atoms necessary to complete a fused benzene ring provided R$^2$ and R$^3$ are taken separately when R$^6$ and R$^7$ are taken together; R$^5$ is selected from hydrogen, hydroxy, alkyl, alkoxy, —N,N—(dialkyl)amino, —N,N—(w-R$^8$alkyl)$_2$—amino wherein R$^8$ is hydroxy or halo, preferably chloro, —NHCOCH$_3$, piperidino, pyrrolidino, N-methylpiperazino, morpholino, thiomorpholino or tetrahydro-2H,4H-1,3,6-dioxazocino; R$^4$, R$^5$ and R$^6$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide; and Y has the same meaning given in formula II.

Usually, the alkyl and alkoxy substituents comprising R$^1$, R$^2$, R$^3$, R$^4$, R$^5$, R$^6$ and R$^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N—(dialkyl)amino and —N,N—(w-R$^8$alkyl)$_2$—amino substituents comprising R$^5$ usually are lower alkyl having 1 to 4 carbon atoms. Preferred electron-withdrawing groups, Y, include cyano; —SO$_2$CH$_3$;

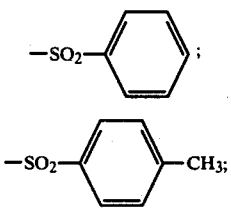

—COCH$_3$; and —SO$_2$N(CH$_2$Ph)$_2$. The sigma value for these and other groups have been reported by Eugen Muller, Methoden Der Organischen Chemie, Georg Thieme Verlag, Stuttgart, 1970, p. 78.

In a particularly preferred embodiment, X in formula (III) above represents the atoms necessary to complete 2,3-dihydrobenz[d]isothiazole-1,1-dioxide.

Specific examples of compounds within the scope of the present invention are as follows:

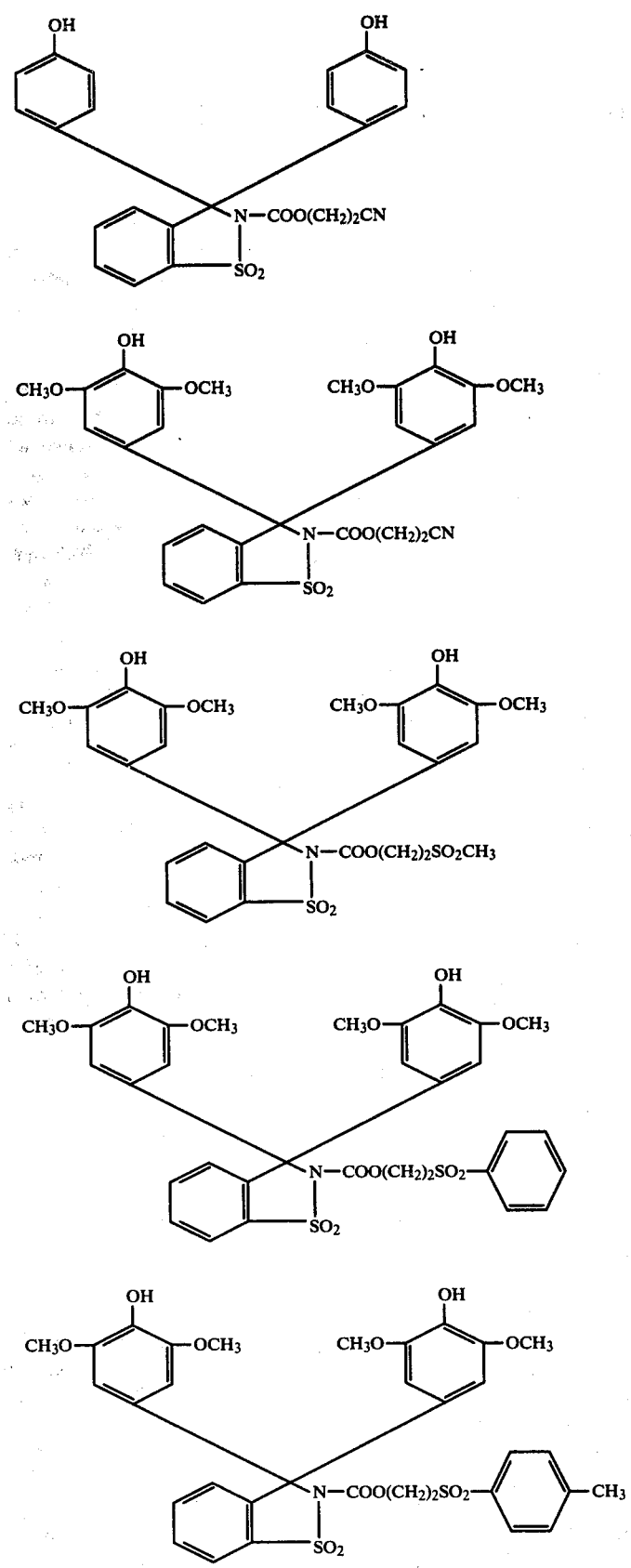

-continued
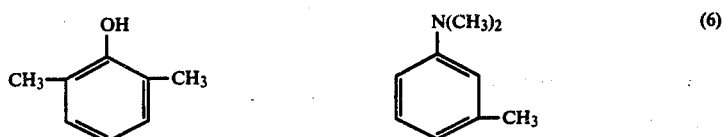
(6)
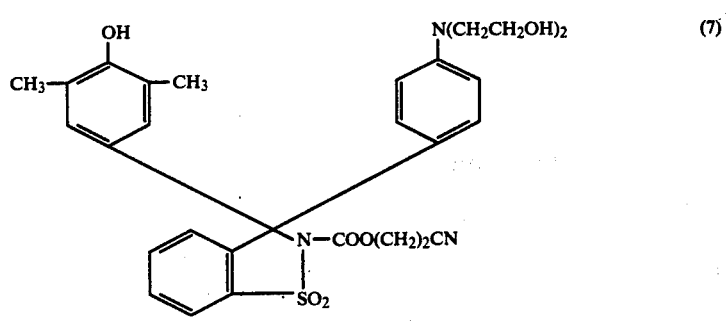
(7)
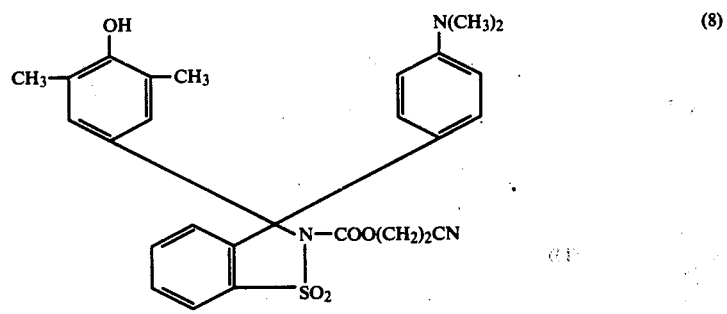
(8)
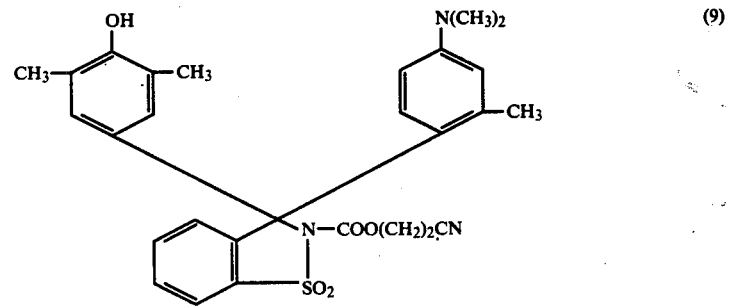
(9)
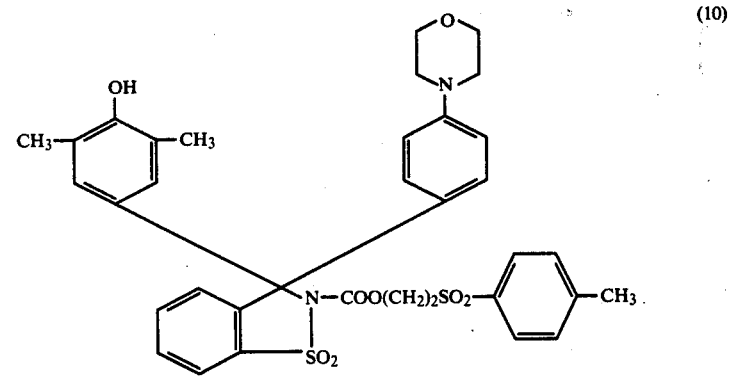
(10)

-continued
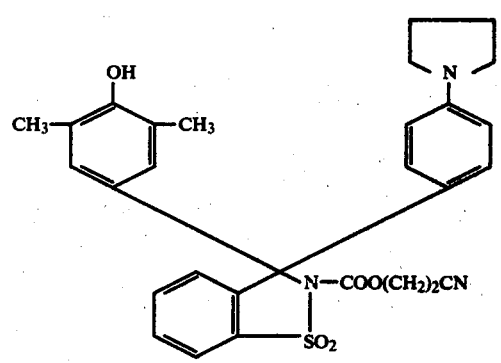
(11)
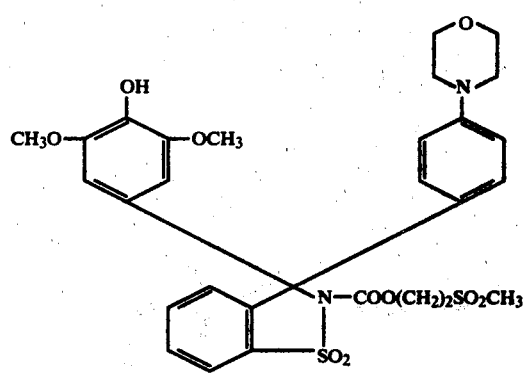
(12)
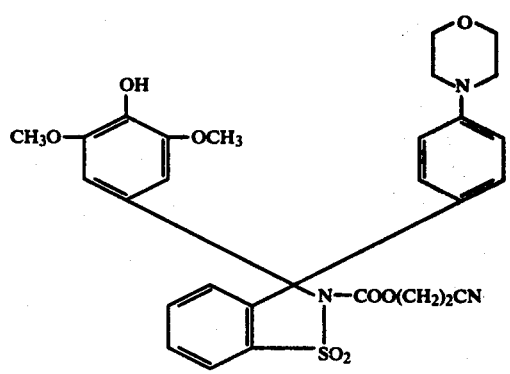
(13)
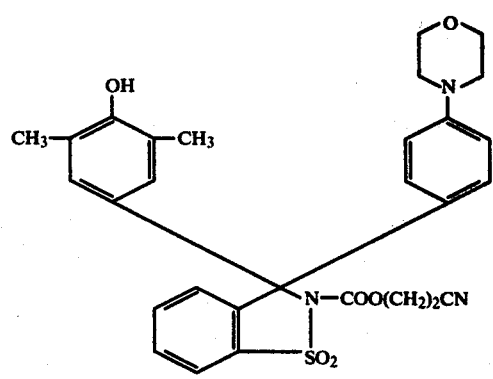
(14)

-continued
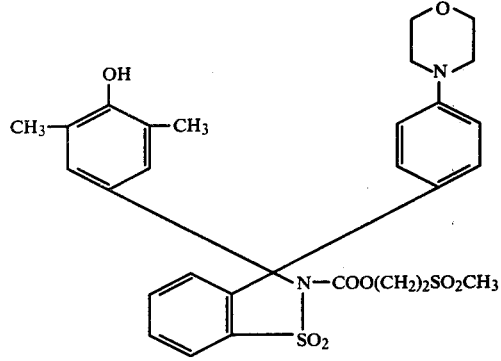
(15)
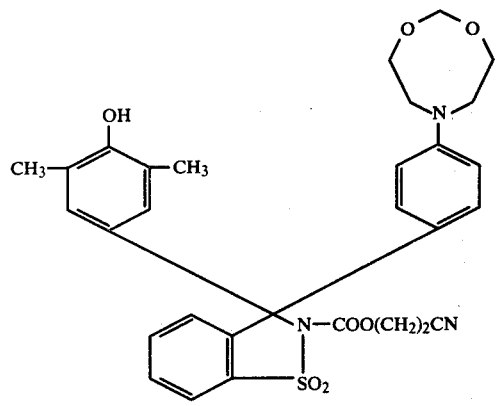
(16)
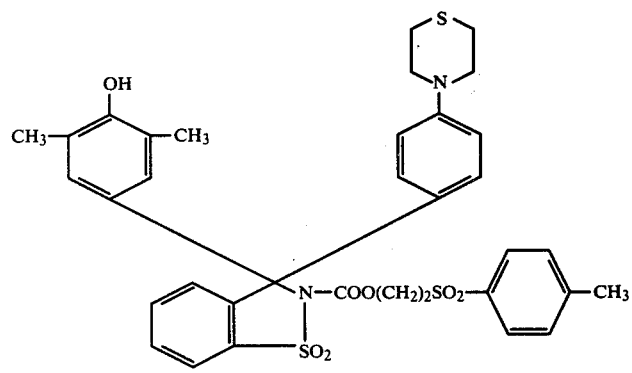
(17)
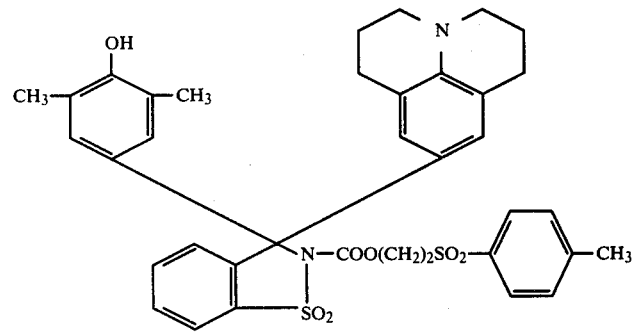
(18)

-continued
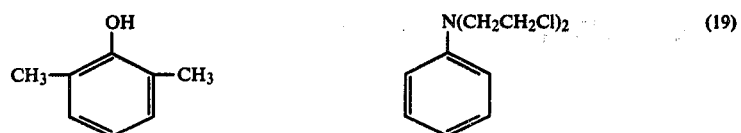 (19)
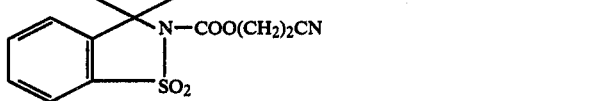 (20)
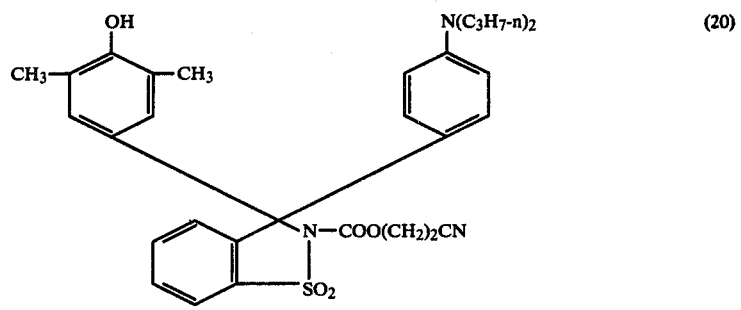 (21)
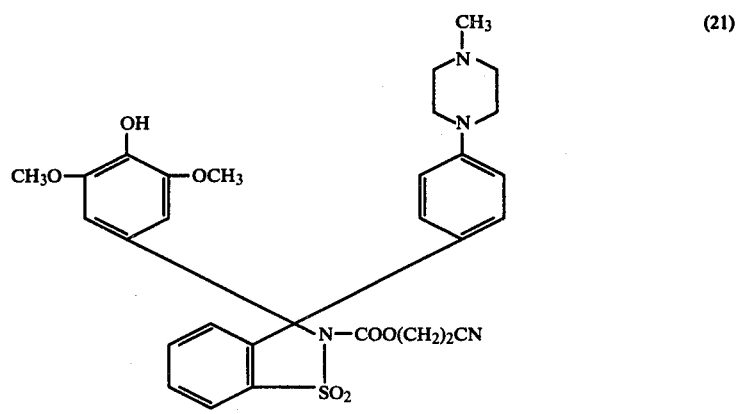 (22)
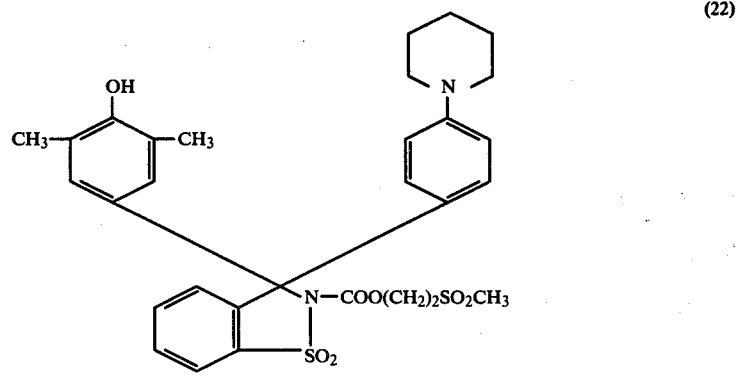 (23)

-continued
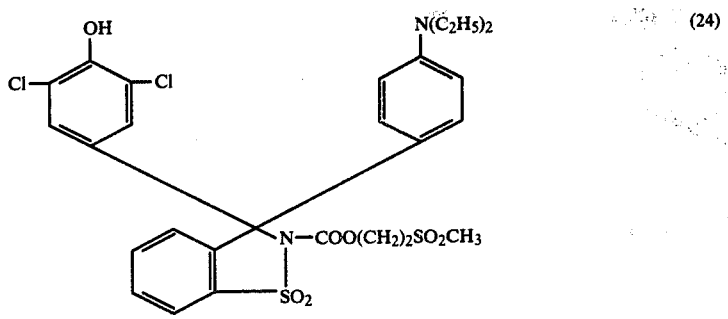
(24)
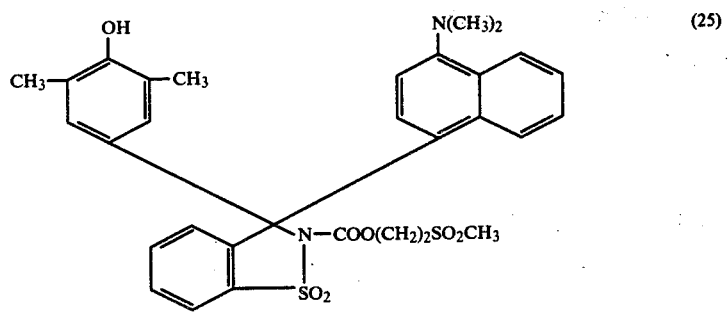
(25)
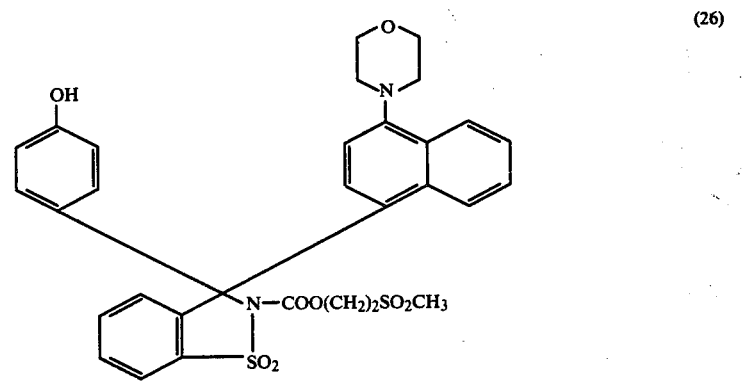
(26)
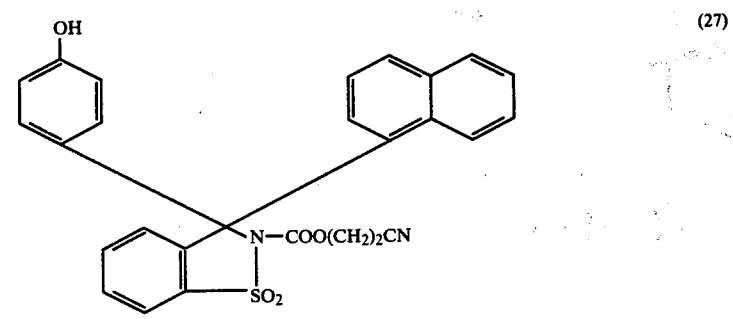
(27)
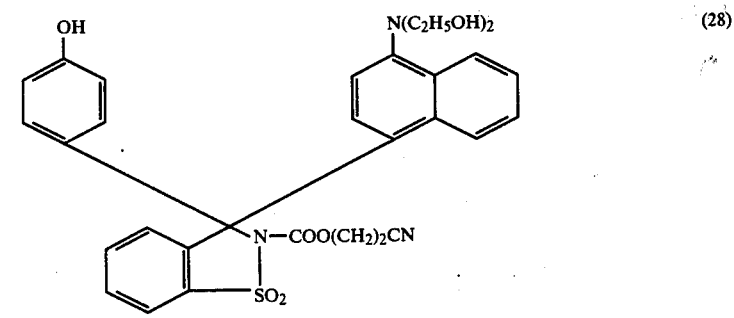
(28)

-continued
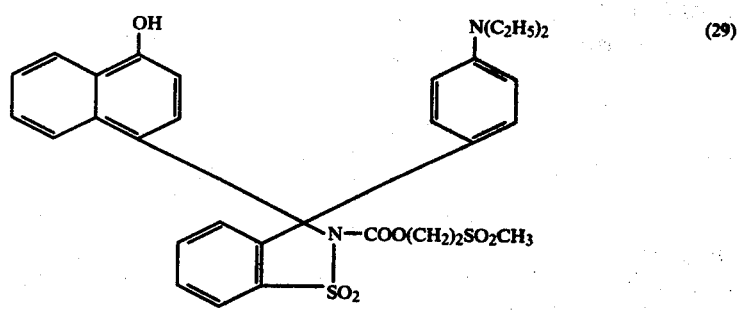 (29)
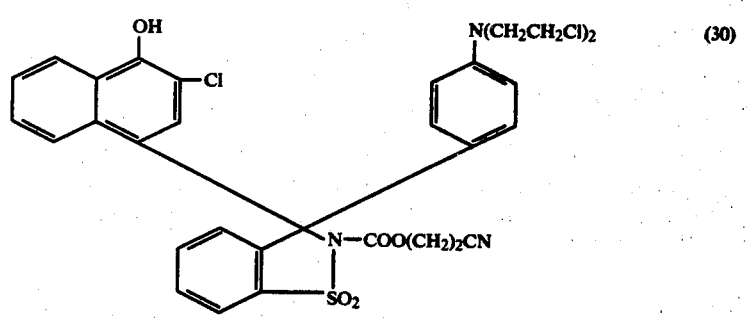 (30)
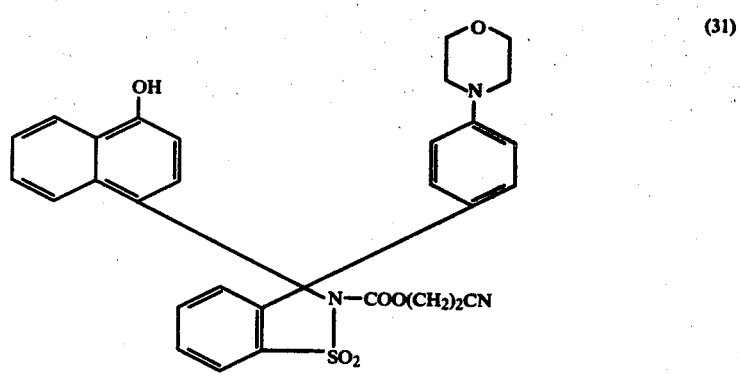 (31)
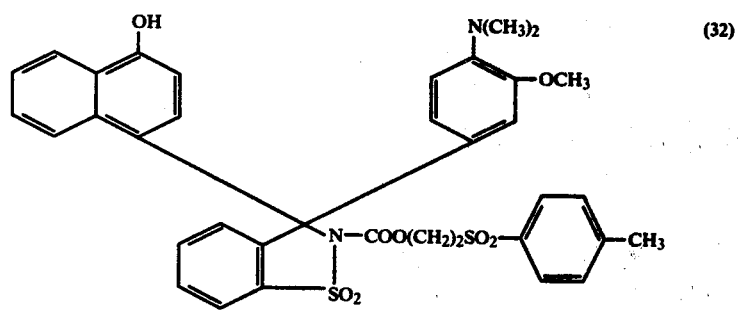 (32)
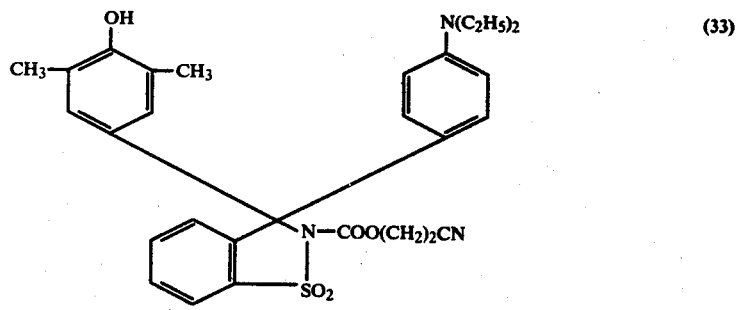 (33)

-continued
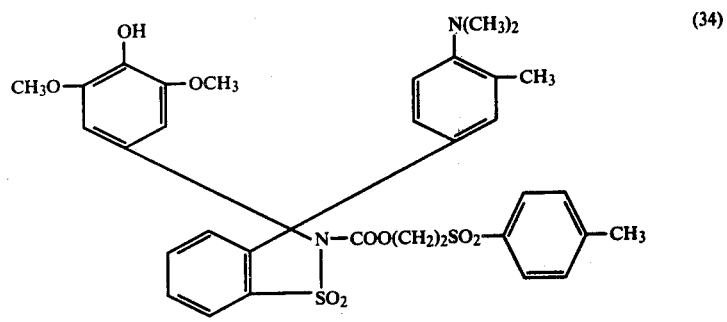
(34)
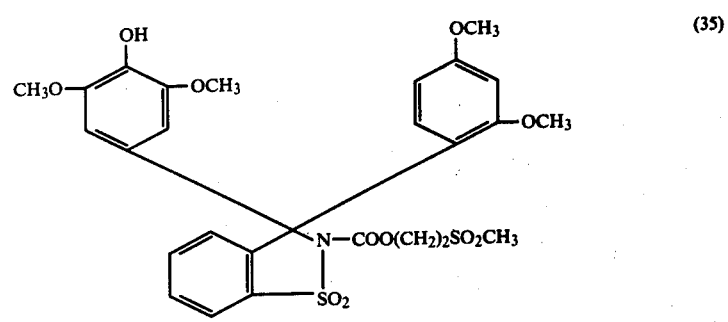
(35)
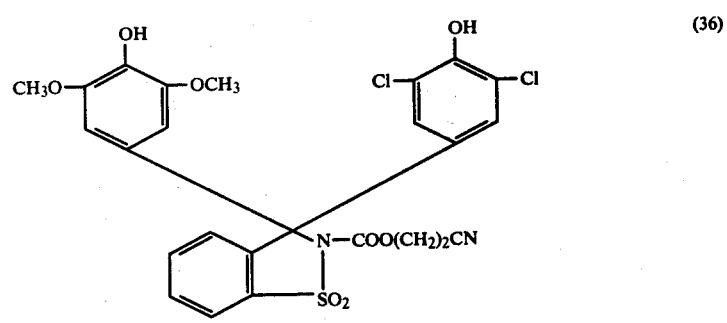
(36)
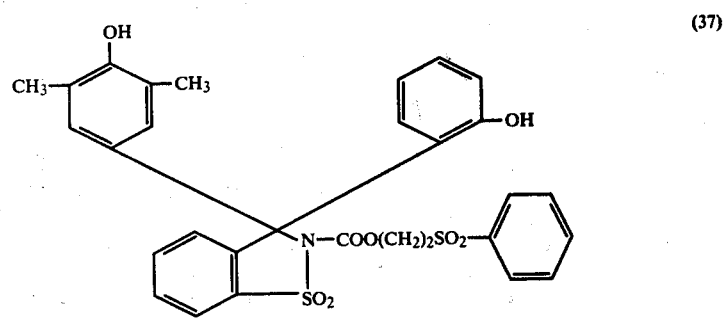
(37)
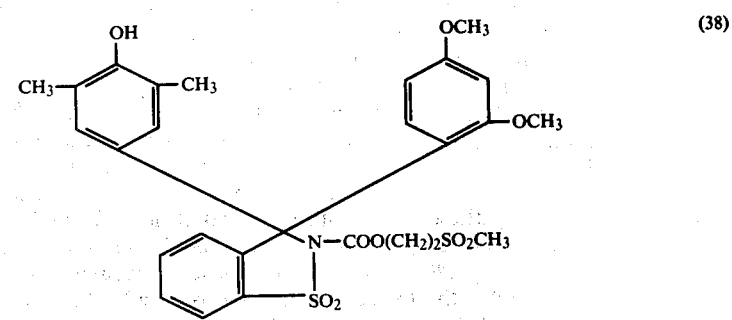
(38)

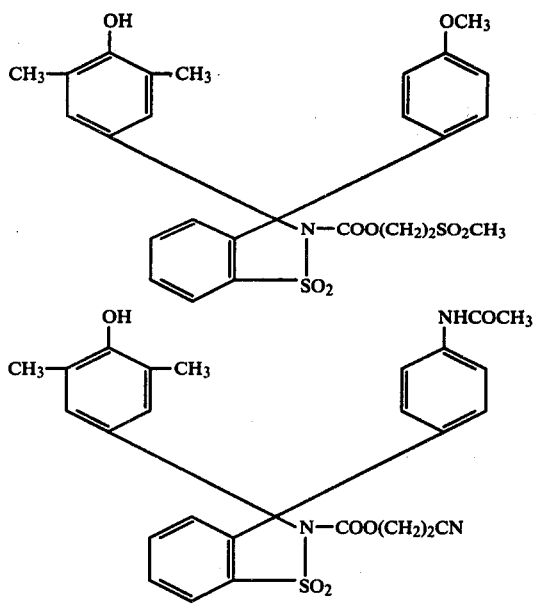

-continued (39)

(40)

The compounds of the present invention may be prepared by reacting (a) a 3-(4'-OP-1'-phenyl/4'-OP-1'-naphthyl)-3-(phenyl/naphthyl)-2,3-dihydrobenz[d]isothiazole-1,1-dioxide wherein P is a protecting group compatible with organometallic reagents and (b) an acylating agent,

wherein W is chloro or bromo and Y is said electron-withdrawing group in pyridine to give the corresponding

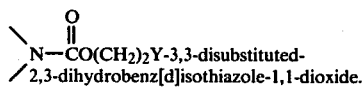

The N-acylated compound is then treated with weak acid to remove the protecting group(s) to yield the 3,3-disubstituted-2,3-dihydrobenz[d]isothiazole-1,1-dioxide product. Optionally, the N-acylation step may be conducted by sequentially reacting (a) with an alkali metal hydride to form the corresponding N-alkali metal salt followed by reaction with the acylating agent. The compounds containing a 2,3-dihydronaphtho[1,8-de]-1,2-thiazine-1,1-dioxide as the ring-closing moiety are prepared by employing a 3-(4'-OP-1'-phenyl/4'-OP-1'-naphthyl)-3-(phenyl/naphthyl)-2,3-dihydro naphtho[1,8-de]-1,2-thiazine-1,1-dioxide in the foregoing procedure. The above described method of synthesizing the compounds of the present invention forms the subject matter of copending U.S. Patent Application Ser. No. 836,010 of Stanley M. Bloom, Alan L. Borror and James W. Foley filed concurrently herewith.

The 3-(4'-OP-1'-phenyl/4'-OP-1'-naphthyl)-3-(phenyl/naphthyl)-2,3-dihydrobenz[d]isothiazole-1,1-dioxides employed as the intermediates, (a), in the above method may be synthesized by reacting a 3-(4'-OP-1'-phenyl/4'-OP-1'-naphthyl)-benz[d]isothiazole-1,1-dioxide and a phenyllithium or a naphthyllithium reagent as disclosed and claimed in copending U.S. Patent Application Ser. No. 836,008 of Alan L. Borror, Louis Cincotta, James W. Foley and Marcis M. Kampe filed concurrently herewith. The 3-(4'-OP-1'-phenyl/4'-OP-1'-naphthyl)benz[d]isothiazole-1,1-dioxide is prepared by converting a blocked 4-halophenol or a blocked 4-halo-1-naphthol to the corresponding Grignard or lithium reagent and then reacting this reagent with saccharin or saccharin pseudo-chloride. 3-(4'-OP-1'-phenyl/4'-OP-1'-naphthyl)benz[d]isothiazole-1,1-dioxides form the subject matter of copending U.S. Patent Application Ser. No. 836,024 of Alan L. Borror, Louis Cincotta, Ernest W. Ellis, James W. Foley and Marcis M. Kampe filed concurrently herewith.

The method of aforementioned application Ser. No. 836,008 is useful in synthesizing intermediates for the subject compounds wherein the A and B moieties are either the same or different. Intermediates for the subject compounds wherein the A and B moieties are the same, i.e., identical, also may be prepared by reacting two equivalents of a blocked phenol (or blocked 1-naphthol) as a Grignard reagent with one equivalent of 3-chlorobenz[d]isothiazole-1,1-dioxide (or 3-chloronaphtho[1,8-de]-1,2-thiazine-1,1-dioxide) as disclosed and claimed in copending U.S. Patent Application Ser. No. 836,004 of Stanley M. Bloom, Alan L. Borror and James W. Foley filed concurrently herewith.

As discussed in the aforementioned applications, the protecting groups selected for preparing the blocked phenols or 1-naphthols and for blocking other substituents as may be necessary should be compatible with lithium and Grignard reagents and should protect the hydroxyl and other groups against reaction under conditions encountered in the synthesis of the starting materials and the intermediates and in the subsequent steps in the synthesis of the products. In addition, the protecting group(s) selected should be capable of being easily removed under neutral or weakly acid conditions to regenerate the hydroxyl and other groups and yield the desired product.

For convenience, the specifications of aforementioned applications Ser. Nos. 836,004, 836,008, 836,024, and 836,010 are incorporated herein.

The following examples are given to further illustrate the present invention and are not intended to limit the scope thereof.

EXAMPLE 1

Preparation of the compound having the formula:

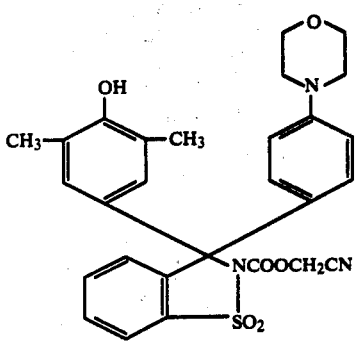

(a) N-(p-bromophenyl)morpholine (0.4 g.) was added to 20 ml. of tetrahydrofuran (THF) and the solution cooled to −65° C. To the solution was added 0.69 ml. of 2.4 M butyllithium in hexane with stirring and stirring was continued for 1 hour. (After 15 minutes the solution became cloudy and a white precipitate formed.) To this solution was added 0.5 g. of 3-(3′,5′-dimethyl-4′-methoxymethoxy-1′-phenyl)benz[d]-isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over Na₂SO₄ and evaporated leaving an oil. The oil was taken up in ligroin (boiling range 30°–60° C.) and refluxed for 1 hour. The white solid that formed was collected to give 0.7 g. of 3-(3′,5′-dimethyl-4′-methoxymethoxy-1′-phenyl)-3-(4″-N-morpholinyl-1″-phenyl)-2,3-dihydrobenz[d]-isothiazole-1,1-dioxide having the formula:

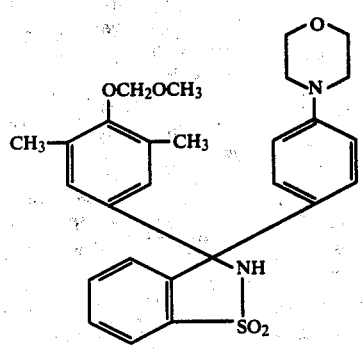

(b) The compound prepared in step (a) (0.7 g.) was placed in 20 ml. of pyridine under nitrogen and 0.15 ml. of β-cyanoethylchloroformate (ClCO₂CH₂CH₂CN) was added to the pyridine solution. The resulting reaction solution was stirred 1 hour, warmed gently and then poured into 100 ml. of water and extracted with chloroform. The chloroform was dried over Na₂SO₄, evaporated and the solid that formed was extracted with ligroin (boiling range 30°–60° C.). The solid obtained was the N-acylated compound, 3-(3′,5′-dimethyl-4′-methoxymethoxy-1′-phenyl)-3-(4″-N-morpholinyl-1″-phenyl)-2-(β-cyanocarbethoxy)-2,3-dihydrobenz[d]isothiazole-1,1-dioxide having the formula:

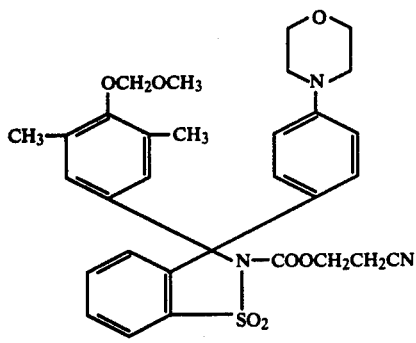

(c) The compound obtained in step (b) was then dissolved in methanol, made acidic with conc. hydrochloric acid and refluxed 1 hour. TLC from ether on silica gel showed 4 spots. The methanol solution was evaporated to leave 0.6 g. of solid. 200 mg. of solid in ether was placed on silica gel 1000 plates and the dark band was removed after drying plates. Acetone was used to remove the N-acylated product from the silica gel. The acetone was removed, ether added and the solution refluxed. The white solid that formed was recovered by filtration to give the title compound.

The 3-(3′,5′-dimethyl-4′-methoxymethoxy-1′-phenyl)benz[d]isothiazole-1,1-dioxide having the formula:

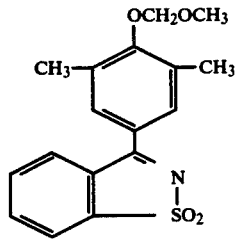

used in step (a) above was prepared as follows:

(i) Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30–45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenyl ether as a colorless oil (boiling point 112° C. and 0.5 mm Hg).

(ii) 4-Bromo-2,6-dimethyl-methylenemethoxyphenyl ether (85.04 g.; 0.347 mole) was dissolved in approximately 800 ml. of tetrahydrofuran. The solution was cooled to −75° C. under a nitrogen blanket, and 2.4 M n-butyllithium in hexane (144.8 ml; 0.346 mole) was added dropwise. Addition was completed within a 2 hour period giving a white slurry.

(iii) Saccharin (61.2 g; 0.334 mole) was dissolved in 600 ml. of dry tetrahydrofuran, and the solution was cooled to approximately −75° C. 2.4 M n-butyllithium in hexane (130.4 ml; 0.311 mole) was slowly added dropwise to the cooled solution under a nitrogen blanket. The temperature was not allowed to rise above −70° C. Addition was completed in about 90 minutes, giving a clear, very pale yellow solution.

(iv) The yellow solution obtained in step (iii) was slowly added (over a 3 hour period) to the white slurry obtained in step (ii) while keeping the temperature at −70° C. During this time the solids disappear giving a clear, caramel colored reaction mixture that first tends to darken with time and then gradually lightens. The reaction mixture was allowed to come to room temperature overnight and then was treated with 36.0 g. of ammonium chloride in 250 ml. of water, while cooling in an ice-water bath. The organic portion was decanted and dried over anhydrous calcium sulfate. The solvent was removed under reduced pressure to give a pink colored oil that became solid on standing in open air. The solid was recrystallized twice from 1-propanol, washed with a 60:40% mixture of petroleum ether-tetrahydrofuran and dried under vacuum to give 68.0 g. of the title compound as a white, crystalline solid.

3-(3′,5′-dimethyl-4′-methoxymethoxy-1′-phenyl)-benz[d]isothiazole-1,1-dioxide also was prepared as follows:

Dry tetrahydrofuran (10–15 ml.) was added to magnesium turnings (0.20 g.) under nitrogen. A solution of 4-bromo-2,6-dimethyl-methylenemethoxyphenyl ether (2.0 g.) in tetrahydrofuran (30 ml.) was added gradually to the magnesium turnings with stirring and heating. After about twenty minutes of external heating to reflux, a self-sustaining reaction was observed. The remaining solution of phenyl ether was then added at a rate to maintain a comfortable reaction. Refluxing with external heating was continued after addition was complete and after one hour, the solution was cooled to room temperature and held under nitrogen. A solution of saccharin pseudo-chloride (1.89 g.) in tetrahydrofuran (40 ml.) was cooled to −78° C. and the previously prepared solution of magnesium bromide reagent was added dropwise to the pseudo-chloride solution under nitrogen. The resulting reaction mixture was stirred cold for about 2 hours and then stirred at room temperature overnight. The reaction mixture was then cooled in an ice water bath and treated with saturated aqueous ammonium chloride solution. The aqueous solution was extracted with chloroform several times and the combined chloroform extracts washed with water and dried over anhydrous sodium sulfate followed by drying over anhydrous calcium sulfate. Upon removing the chloroform, a colorless oil was obtained which was extracted several times with small portions of light petroleum ether to leave behind a pale yellow tacky tar. The yellow tar was treated with ether leaving behind an off-white solid. The off-white solid was dissolved in a small amount of chloroform, treated with carbon black and filtered through Celite. Upon removing the solvent, the title compound was obtained as an off-white solid which was dried under vacuum in the presence of $P_2O_5$. Yield 0.520 g.

3-chlorobenz[d]isothiazole-1,1-dioxide (saccharin pseudo-chloride) was prepared as follows:

35 g. of saccharin and 43.7 g. of $PCl_5$ were heated at 170° C. for 1¼ hours during which time complete solution occurred and $POCl_3$ began to reflux. The $POCL_3$ was removed at reduced pressure to leave a crystalline residue. Diethyl ether was added to the crystalline residue and stirred well. The title compound was recovered as white crystals, 12.5 g. (melting range 146°–147° C.).

The N-(p-bromophenyl)morpholine having the formula

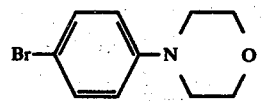

used in step (a) above was prepared as follows:

25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of the title compound as white crystals.

The β-cyanoethylchloroformate having the formula (CNCH₂CH₂COOCl) used in step (b) above was prepared as follows:

To 100 ml. of dry benzene, cooled in an ice bath, was added phosgene gas until 34.0 g. was collected. Hydroxyacrylonitrile (20.2 g.) was added to the cooled phosgene solution. (The temperature rose slightly to approximately 8° C.) The resulting heterogeneous mixture was cooled to 3° C. with stirring, and pyridine (22.6 g.) in 25 mls. of benzene was added dropwise. Heat was evolved, and the temperature was not allowed to rise above 10° C. Very vigorous stirring was maintained until solid began to form. After about 1 hour, the reaction mixture was stirred at approximately 5° C. for 15 minutes, then allowed to come to 15° C.–20° C. and stirred for another 15 minutes. The reaction mixture was then cooled to 5° C. and 26 ml. of ice water was added in increments. The solids dissolved with liberation of heat and evolution of gas. The temperature was not allowed to rise above 15° C. over the next 15–20 minutes. The reaction mixture was then stirred at room temperature for 2 hours, the benzene layer decanted and dried over anhydrous $Na_2SO_4$, followed by drying over anhydrous $CaSO_4$. The solvent was removed under reduced pressure to yield an almost colorless oil which was redistilled under vacuum at a boiling range of 68.5°–70.5° C. (pot temperature 98°–103° C.) to yield 18.2 g. of the title compound as a colorless oil.

EXAMPLES 2 and 3

The compounds having the formulas

Example 2

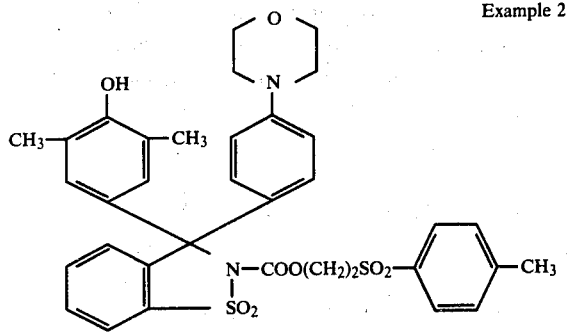

Example 3

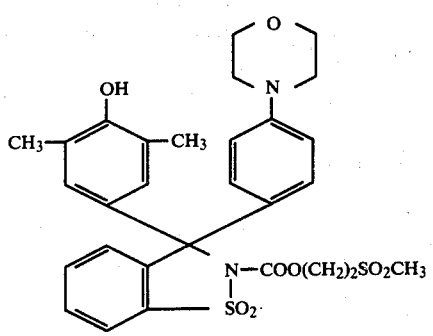

were prepared in the same manner described in Example 1 except that the 3-(3',5'-dimethyl-4'-methoxymethoxy-1'-phenyl)-3-(4''-N-morpholinyl-1'''-phenyl)2,3-dihydrobenz[d]isothiazole-1,1-dioxide was reacted in step (b) with the appropriate acylating agents, namely,

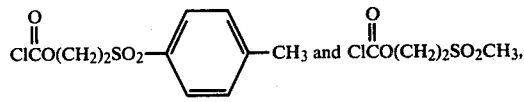

to yield the corresponding N-acylated compounds which were treated as in step (c) above to remove the protecting groups.

EXAMPLE 4

Preparation of the compound having the formula

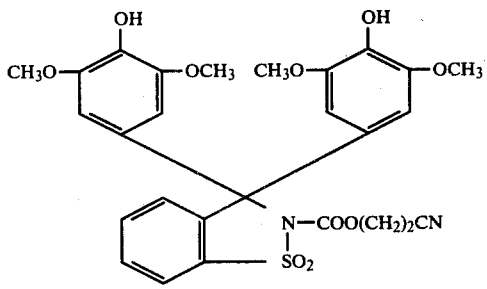

(a) 55 g. of 4-bromo-2,6-dimethoxy-methylenemethoxyphenyl ether was dissolved in 300 ml. of anhydrous tetrahydrofuran under a stream of nitrogen. The solution was cooled to −65° C. during which time some of the phenyl ether precipitated. To this was added 79 ml. of butyl-lithium (2.4 M in hexane) at a range to keep the temperature below −50° C. The resulting solution was cooled to −65° C. and was stirred for 30 minutes. To this solution was added 19 g. of saccharin pseudochloride in two portions so as to keep the temperature below −40° C. The reaction solution was cooled to −65° C. and was stirred for 40 minutes. TLC showed one main spot on silica gel with 10 ml. ether/2 drops methanol. The reaction solution was poured into 2000 ml. of water and made acidic to pH 6. The mixture changed color from orange to yellow at this pH. The mixture was extracted two times with ether (2 liters) and the ether washed with water. The ether was dried over sodium sulfate and evaporated to leave a light yellow solid. The solid was recrystallized from 450 ml. of n-propanol to give 42 g. of 3,3-di(3',5'-dimethoxy-4'-methoxymethoxy-1'-phenyl)-2,3-dihydrobenz[d]isothiazole-1,1-dioxide as off-white crystals (melting range 151.5°–152.5° C.).

(b) The compound prepared in step (a) (27.0 g.) was dissolved in 125 ml. of dioxane at room temperature under nitrogen. To this solution was added 2.50 g. of NaH (57% oil dispersion) and the resulting dispersion stirred for 45 minutes. (Evolution of hydrogen was observed.) Then 8.0 ml. of ClCOOCH$_2$CH$_2$CN was added and an exotherm resulted. The resulting reaction mixture was stirred for 3 hours. The initial yellow color disappeared and a white dispersion formed. This dispersion was poured into 2 liters of water, made neutral with dilute HCl and extracted with chloroform. The chloroform was washed with water, separated, dried over sodium sulfate, and evaporated to yield a white solid. The solid was stirred with ethyl ether, isolated by filtration, dried in vacuo, and crystallized from methanol. The white needles that formed were recovered by filtration to give the N—COOCH$_2$CH$_2$CN derivative of 3,3-di(3',5'-dimethoxy-4'-methoxymethoxy-1'-phenyl)-2,3-dihydrobenz[d]isothiazole-1,1-dioxide.

(c) 3.7 g. of 3,3-di(3',5'-dimethoxy-4'-methoxymethoxy-1'-phenyl)-2-β-cyanocarbethoxy-2,3-dihydrobenz[d]isothiazole-1,1-dioxide prepared as in step (b) above was placed in 200 ml. of methanol and 2 drops of HCl were added. The resulting solution was refluxed and the reaction was followed by TLC on silica gel with ether. When TLC indicated that no more blocked compound remained, the reaction was discontinued and the methanol removed in vacuo to leave an egg-white solid (3.2 g.). This was dissolved in 80 ml. of 1,2-dichloroethane with heating and 80 ml. of petroleum ether was added with swirling. The solution was cooled and the light beige crystals that formed were collected and dissolved in 175 ml. of ethanol at reflux. The ethanol solution was allowed to cool in the refrigerator overnight and 2.7 g. of the title compound was collected as white needles (melting range 191°–193° C.).

The methoxymethylation of 4-bromo-2,6-dimethoxyphenol was carried out as follows:

To a 3 liter flask was added 300 g. of P$_2$O$_5$ under nitrogen and 800 ml. of chloroform (previously dried over P$_2$O$_5$). The mixture was cooled to −15° C. with a dry-ice acetone bath and then 50 g. of 4-bromo-2,6-dimethoxyphenol in 800 ml. of dimethoxymethane was added over a 25 minute period while maintaining the temperature at −15° C. or below. To the resulting reaction mixture was added 1 ml. of conc. sulfuric acid and then the temperature was allowed to come to room temperature. During this time, a tacky mass of P$_2$O$_5$ developed. The reaction mixture was stirred for 3 hours. TLC indicated that the reaction was complete. The chloroform was then decanted into 400 ml. of 10% aqueous sodium hydroxide, stirred well and the chloroform layer separated, washed with water, dried over Na₂SO₄ and evaporated to leave light tan crystals. n-Propanol was added to the crystalline residue, stirred and filtered to give 32.7 g. of the title compound as white crystals (melting range 98°-100° C.).

EXAMPLES 5 and 6

The compounds having the formulas

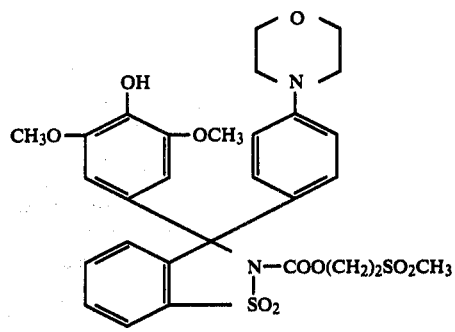
Example 5

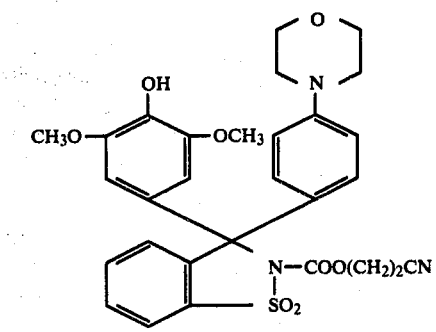
Example 6 were prepared according to the procedure described in Example 1 except that 3-(3',5'-dimethoxy-4'-methoxymethoxy-1'-phenyl)benz[d]isothiazole-1,1-dioxide was used in the reaction of step (a) and the appropriate acylating agents, namely,

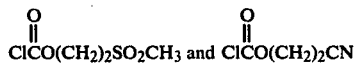

were used in step (b).

The 3-(3',5'-dimethoxy-4'-methoxymethoxy-1'-phenyl)benz[d]isothiazole-1,1-dioxide used in step (a) above was prepared as follows:

(i) Using an 18 gauge needle-syringe, 20.0 mls. of n-butyllithium (2.4 M in hexane) was added dropwise over 1 hour to a solution of 9.16 g. of saccharin (previously dried overnight at 80° C. in vacuo) in 250 mls. of dry tetrahydrofuran under nitrogen at −75° C. to −73° C. with rapid stirring. The reaction solution comprising the N-lithium salt of saccharin in tetrahydrofuran was used directly in step (iii) without isolating the lithium salt.

(ii) In a dried 1 l. flask, 13.86 g. of 4-bromo-2,6-dimethoxy-methylenemethoxyphenyl ether was dissolved in 300 mls. of dry tetrahydrofuran under nitrogen, and 20.83 mls. of n-butyllithium (2.4 M in hexane) was added dropwise with stirring at −75° C. After addition was complete, the reaction solution was stirred at −75° C. for about 30 minutes.

(iii) The solution of saccharin lithium salt prepared in step (i) was transferred to an addition funnel using a double-tip needle under nitrogen pressure and added to the solution of 4-Li-2,6-dimethoxy-methylenemethoxyphenyl ether prepared in step (ii) over about 15 minutes with stirring at a temperature of −75° C. to −70° C. The reaction mixture was stirred for about 2 hours at −75° C. and then warmed to 0° C. during an hour.

(iv) A solution of 5.2 g. of ammonium chloride in 175 mls. of water was added dropwise to the reaction mixture of step (iii) and the reaction mixture was transferred to a 1 l. separatory funnel. After the two phases separated, the aqueous phase was removed and the pH was lowered from about 11 to about 6-7 by the dropwise addition of aqueous 5% hydrochloric acid solution. (A color change from yellow to colorless was observed.) The aqueous phase was returned to the separatory funnel, partitioned and the aqueous phase again separated and then extracted with fresh ether (100 mls.). The ether and tetrahydrofuran/hexane extracts were combined, dried over magnesium sulfate overnight, filtered and the solvent removed to leave a yellow oil which crystallized. Ether (100 mls.) was added to the crystalline material and the crystalline material was ground under ether in a mortar, filtered, washed with more ether followed by petroleum ether and air dried. A second crop was collected from the filtrate to give a total yield of 13.0 g. of the title compound.

EXAMPLES 7-11

The compounds having the formulas:

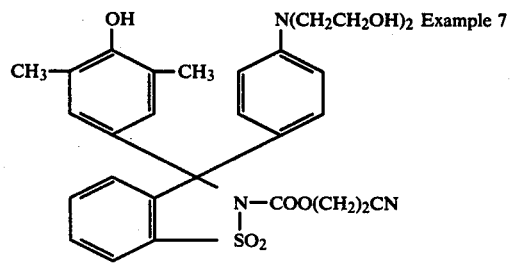
Example 7

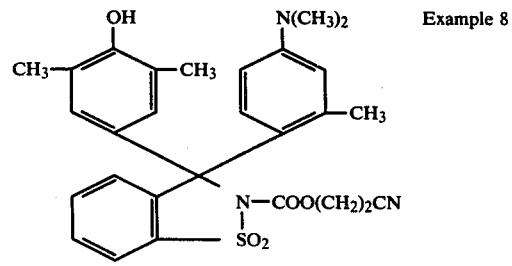
Example 8

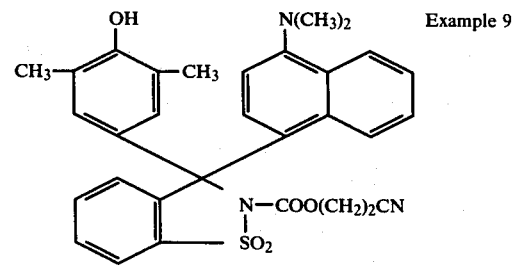
Example 9

Example 10

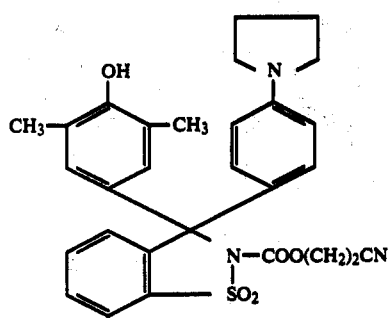

Example 11

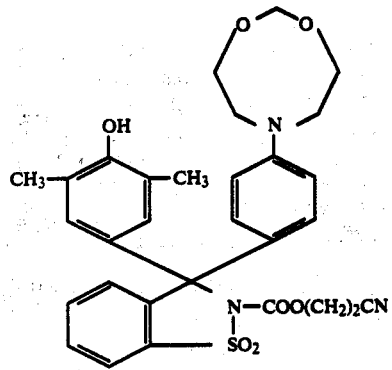

were prepared according to the procedure given in Example 1 except that in step (a) the 3-(3',5'-dimethyl-4'-methoxymethoxy-1'-phenyl)benz[d]isothiazole-1,1-dioxide was reacted with the appropriate lithium reagent, namely,

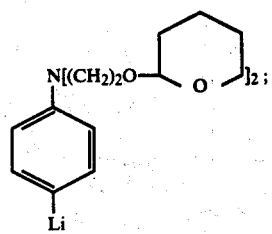 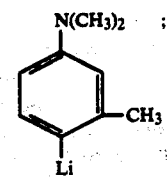

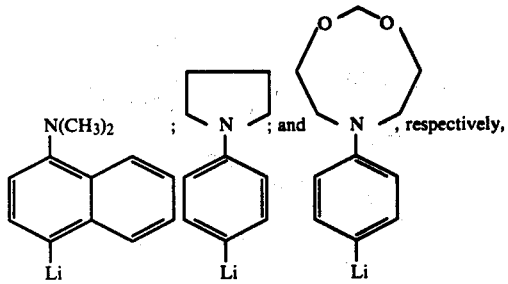 respectively, and the 2'-tetrahydropyranyl groups were removed from the protected N,N-di(β-hydroxyethyl)anilino moiety of Example 7 in step (c) simultaneously with the 4'-methoxymethyl protecting group.

N-(p-Li-phenyl)tetrahydro-2H,4H-1,3,6-dioxazocine may be prepared by reacting the corresponding p-halophenyl compound with n-butyllithium. The N-(p-halophenyl)tetrahydro-2H,4H-1,3,6-dioxazocines are prepared by reacting p-halo-N,N'-di(β-hydroxyethyl)aniline with certain dihalomethanes in the presence of a solid alkali metal hydroxide or concentrated aqueous solution thereof and a quaternary ammonium salt. These compounds and their preparation form the subject matter of U.S. Patent Application Ser. No. 836,066 of Louis Cincotta, James W. Foley and Marcis M. Kampe filed concurrently herewith.

EXAMPLES 12–14

The compounds having the formulas

Example 12

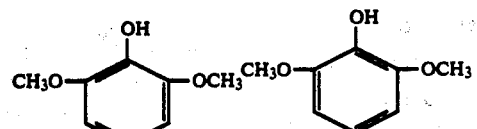

Example 13

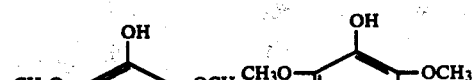

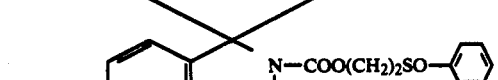

Example 14

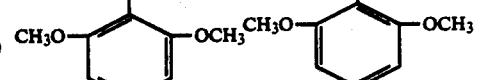

were prepared in the same manner described in Example 4 except that the acylating agents employed were

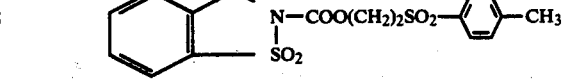 and

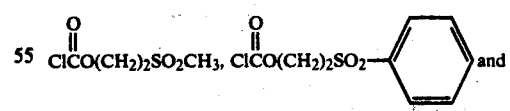

respectively.

EXAMPLE 15

Preparation of the compound having the formula:

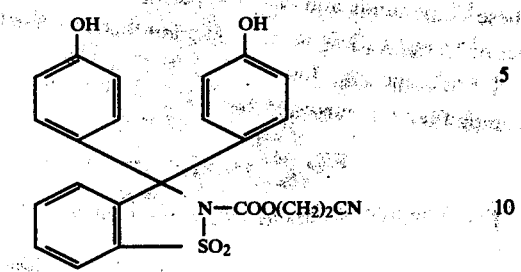

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

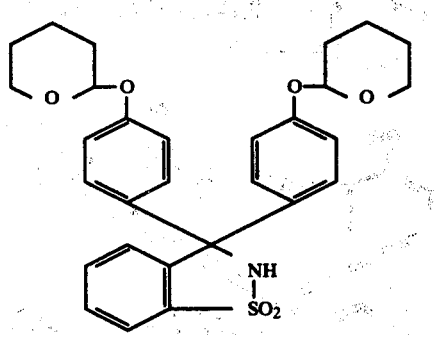

A (b) Compound A as prepared in step (a) (10.0 g.) was placed in 100 ml. of dioxane and 0.88 g. of sodium hydride (as 57% oil dispersion) was added at room temperature under nitrogen (hydrogen evolution was observed). The resultant mixture comprising the N-sodium salt of the above compound was stirred 1 hour and then 2.4 ml. of ClCOOCH$_2$CH$_2$CN was added. A white precipitate formed immediately. The reaction mixture was stirred overnight, then poured into 200 ml. water. The aqueous mixture was extracted with three 250 ml. portions of ether, which were combined and dried over sodium sulfate. The ether was removed in vacuo and the resulting solid washed with petroleum ether. Upon drying, 10.5 g. of the crude N-acylated derivative was obtained. The N-acylated compound has the formula

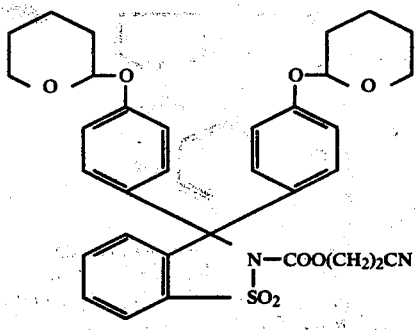

B (c) Compound B (5.0 g.) as prepared in step (b) was dissolved in 50 ml. of warm methanol which contained two drops of conc. HCl. This solution was allowed to stand at room temperature for 30 min. at which time the analysis indicated both tetrahydropyranyl protecting groups had been removed. The methanol and HCl were removed in vacuo leaving 5.0 g. of a light yellow solid which was fractionated via column chromatography (silica gel; ether) to give a pure sample of the title compound.

Tetrahydropyranylation of p-bromo-phenol used in the preparation of compound A was carried out as follows:

To 10.5 ml. of dihydropyran containing 2 drops of conc. HCl was added 10.0 g. of p-bromophenol. (The reaction was exothermic; temperature rose to 35° C.). After the addition was completed, the colorless solution obtained was heated to 50° C. and allowed to cool with stirring for 1 hour. The solution was extracted with 20 ml. of ether and 10 ml. of 10% NaOH. The ether layer was dried over anhydrous Na$_2$SO$_4$ and evaporated under reduced pressure to leave an oil. 80 ml. of ethanol was added to the oil and the resulting ethanol solution was allowed to stand. The white crystals that formed were recovered by filtration and dried under vacuum to yield 7.3 g. of the blocked phenol. The mother liquor was concentrated to one-half its original volume and cooled. More crystals formed which were isolated to yield an additional 2.1 g. of blocked phenol.

The intermediates having the formulas:

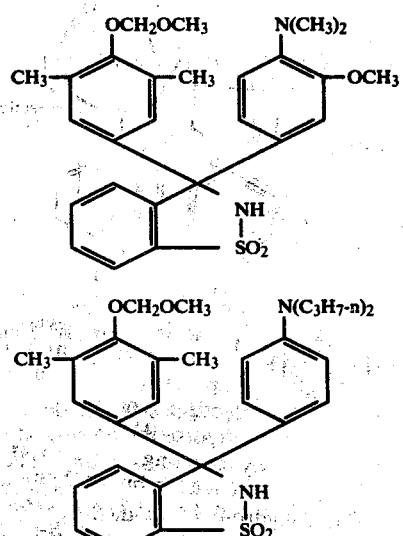

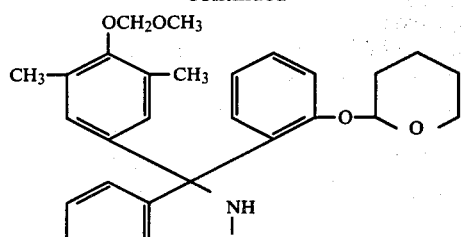
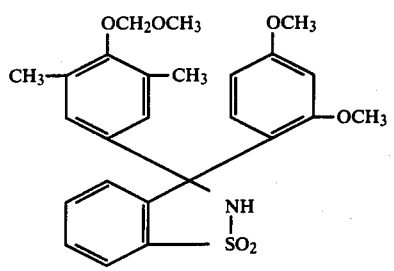
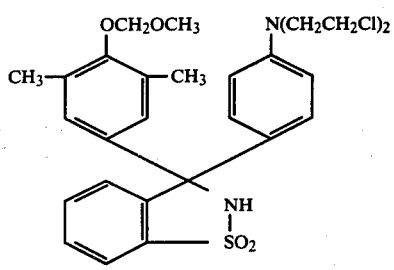
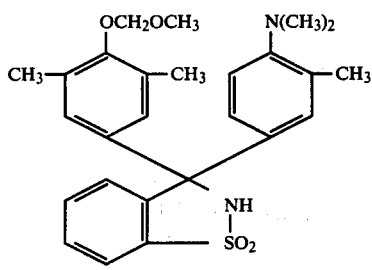
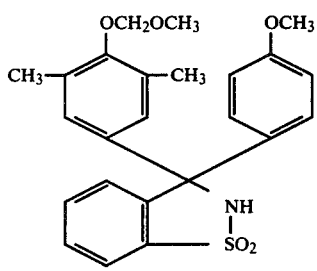
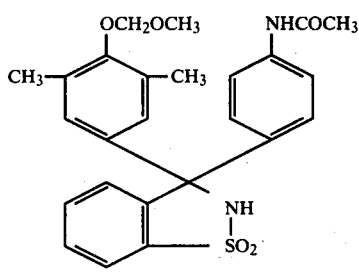
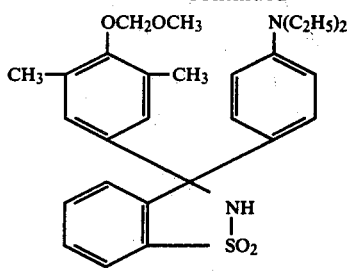
were prepared by reacting 3-(3',5'-dimethyl-4'-methoxymethoxy-1'-phenyl)benz[d]isothiazole-1,1-dioxide with the selected aryl lithium reagent as described in step (a) of Example 1 above. The lithium reagents employed were
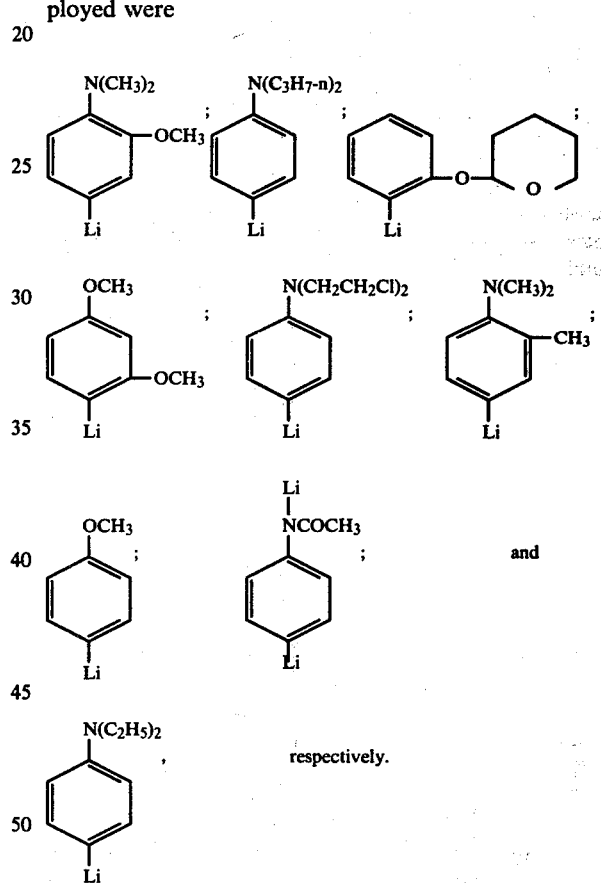
respectively.
The intermediates having the formulas:
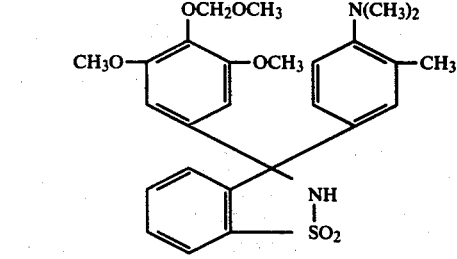

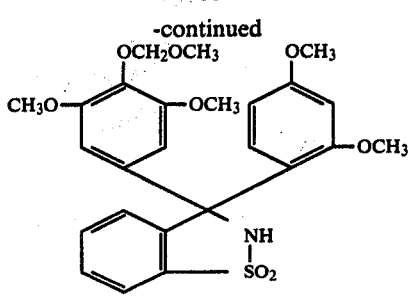

were prepared according to the procedure given in step (a) of Examples 5 and 6 by reacting 3-(3',5'-dimethoxy-4'-methoxymethoxy-1'-phenyl)benz[d]isothiazole-1,1-dioxide with the appropriate lithium reagent, namely,

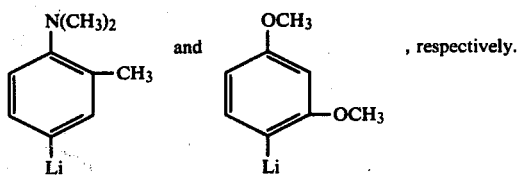, respectively.

It will be appreciated that using the procedures described in the foregoing Examples, the above intermediates may be reacted with an acylating agent of the formula

wherein W and Y have the same meaning given previously to yield the corresponding

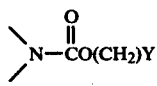

compounds which compounds may be treated with weak acid to remove the protecting group(s) and give the respective products.

Also, it will be appreciated that 1-naphthols may be substituted for phenols in the procedures described in the foregoing examples to give the corresponding 4'-hydroxy-1'-naphthyl compounds. For example, the methoxymethyl ether and the 2'-tetrahydropyranyl ether of 4-bromo-1-naphthol were prepared according to the methoxymethylation and tetrahydropyranylation procedures described above followed by conversion to the corresponding 4-lithium derivatives by reaction with n-butyllithium also as described above. The lithium derivatives may be reacted with the N-lithium salt of saccharin to give the corresponding 3-(4'-OP-1'-naphthyl)benz[d]isothiazole-1,1-dioxide which, in turn, may be reacted with the selected phenyllithium reagent to give the corresponding 3-(4'-OP-1'-naphthyl)-3-(phenyl)-2,3-dihydrobenz[d]isothiazole-1,1-dioxide.

Where it is desired to prepare sulfamnaphthaleins, 2,3-dihydro-3-oxo-naphtho[1,8-de]1,2-thiazine-1,1-dioxide or its pseudo chloride may be substituted for the saccharin reagents used in the foregoing Examples to give the corresponding sulfamnaphthalein intermediates and products. The pseudo-chloride may be prepared from the 3-oxo thiazine by reaction with $PCl_5$ as described above for the preparation of saccharin pseudo-chloride.

As noted above, the compounds of the present invention are useful in photographic products and processes as colorless precursors for providing colored optical filter agents for protecting an imagewise exposed photosensitive material from further exposure during processing in light. The use of the subject compounds as photographic optical filter agents and filter agent precursors is disclosed and claimed in copending U.S. Patent application Ser. No. 836,006 of Stanley M Bloom, Alan L. Borror and James W. Foley filed concurrently herewith. For convenience, the specification of this application is specifically incorporated herein.

As discussed in the aforementioned application, the colored optical filter agents generated from precursor compounds possessing a

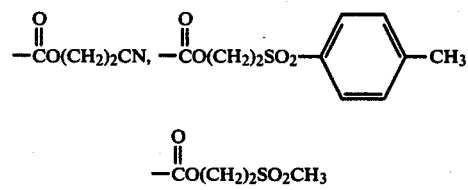

moiety in the 2-position of the benz[d]isothiazole-1,1-dioxide ring have a half-life (T½) in approximately 1 N NaOH of 30 seconds, 14 seconds and 7 seconds, respectively. By T½ is meant the time measured for one-half of the colored species to decolorize.

Figure 2:
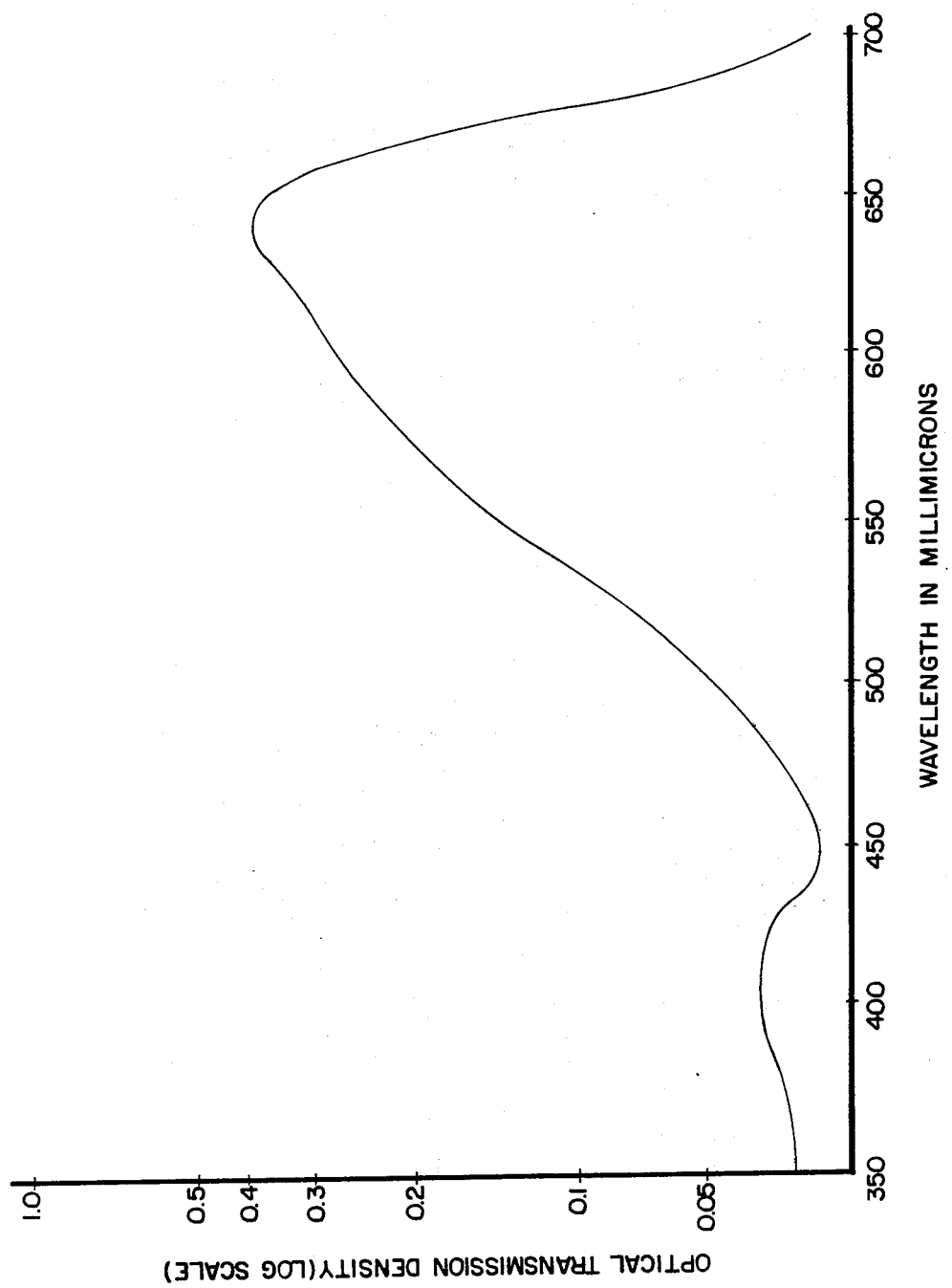

The spectral absorption characteristics of the colored species formed in alkali above pH 10 by compounds possessing di-(3',5'-dimethoxy-4'-hydroxy-1'-phenyl) as the 3,3-substituents as illustrated by the compound of formula (2) and possessing (3',5'-dimethyl-4'-hydroxy-1'-phenyl) and (4"-morpholino-1"-phenyl) as the 3,3-substituents as illustrated by the compound of formula (15) are graphically illustrated in the accompanying FIGS. 1 and 2, respectively.

Since certain changes may be made in the above product and process without departing from the scope of the invention herein involved, it is intended that all matter contained in the above description shall be interpreted as illustrative and not in a limiting sense.

What is claimed is:

1. A compound of the formula

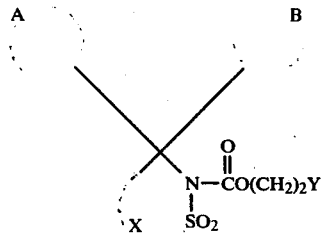

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete 2,3-dihydrobenz[d]isothiazole-1,1-dioxide or 2,3-dihydronaphtho[1,8-de]-1,2-thiazine-1,1-dioxide; and Y is an electron-withdrawing group having a positive sigma value greater than 0.60 as defined by Hammett's Equation.

2. A compound as defined in claim 1 wherein Y is —CN.

3. A compound as defined in claim 1 wherein Y is —SO$_2$CH$_3$.

4. A compound as defined in claim 1 wherein Y is

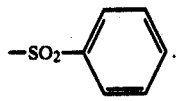.

5. A compound as defined in claim 1 wherein Y is

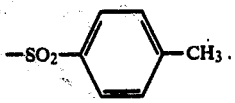.

6. A compound of the formula

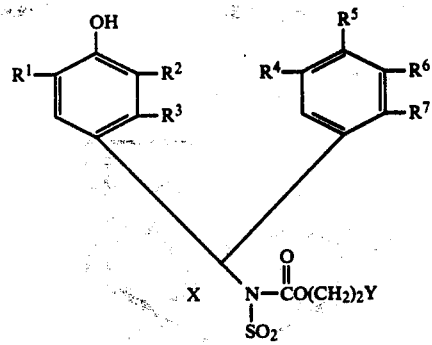

wherein R$^1$ and R$^2$ each are selected from hydrogen, alkyl having 1 to 4 carbon atoms, alkoxy having 1 to 4 carbon atoms; chloro and fluoro; R$^3$ is hydrogen, alkyl having 1 to 4 carbon atoms, alkoxy having 1 to 4 carbon atoms or hydroxy; R$^2$ and R$^3$ taken together represent the carbon atoms necessary to complete a fused benzene ring; R$^4$ and R$^6$ each are selected from hydrogen, alkyl having 1 to 4 carbon atoms, alkoxy having 1 to 4 carbon atoms, chloro and fluoro; R$^7$ is hydrogen, hydroxy, alkyl having 1 to 4 carbon atoms or alkoxy having 1 to 4 carbon atoms; R$^6$ and R$^7$ taken together represent the carbon atoms necessary to complete a fused benzene ring provided R$^2$ and R$^3$ are taken separately when R$^6$ and R$^7$ are taken together; R$^5$ is selected from hydrogen, hydroxy, alkyl having 1 to 4 carbon atoms, alkoxy having 1 to 4 carbon atoms, —N,N—(dialkyl)amino wherein each alkyl contains 1 to 4 carbon atoms, —N,N—(w—R$^8$alkyl)$_2$amino wherein R$^8$ is hydroxy or halo and said alkyl contains 1 to 4 carbon atoms, —NHCOCH$_3$, piperidino, pyrrolidino, N-methylpiperazino, morpholino, thiomorpholino or tetrahydro-2H,4H-1,3,6-dioxazocino; R$^4$, R$^5$ and R$^6$ taken together represent the atoms necessary to complete a fused [ij]-quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide; and Y is an electron-withdrawing group having a positive sigma value greater than 0.60 as defined by Hammett's Equation.

7. A compound as defined in claim 6 wherein Y is —CN.

8. A compound as defined in claim 6 wherein Y is —SO$_2$CH$_3$.

9. A compound as defined in claim 6 wherein Y is

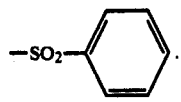.

10. A compound as defined in claim 6 wherein Y is

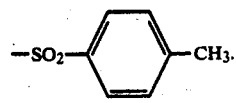.

11. A compound as defined in claim 6 wherein said R$^1$ and R$^2$ each are alkyl.

12. A compound as defined in claim 11 wherein said R$^3$ is hydrogen.

13. A compound as defined in claim 6 wherein said R$^1$ and R$^2$ each are alkoxy.

14. A compound as defined in claim 13 wherein said R$^3$ is hydrogen.

15. A compound as defined in claim 12 wherein said R$^5$ is hydroxy.

16. A compound as defined in claim 15 wherein said R$^4$ and R$^6$ are alkyl and said R$^7$ is hydrogen.

17. A compound as defined in claim 14 wherein said R$^5$ is hydroxy.

18. A compound as defined in claim 17 wherein said R$^4$ and R$^6$ are alkoxy and said R$^7$ is hydrogen.

19. A compound as defined in claim 16 wherein said R$^1$, R$^2$, R$^4$ and R$^6$ each are methyl.

20. A compound as defined in claim 18 wherein said R$^1$, R$^2$, R$^4$ and R$^6$ each are methoxy.

21. A compound as defined in claim 12 wherein said R$^1$ and R$^2$ are methyl and R$^4$, R$^6$ and R$^7$ are hydrogen.

22. A compound as defined in claim 21 wherein said R$^5$ is morpholino.

23. A compound as defined in claim 21 wherein said R$^5$ is —N,N—(dialkyl)amino.

24. A compound as defined in claim 21 wherein said R$^5$ is —N,N—(w—R$^8$alkyl)$_2$amino.

25. A compound as defined in claim 21 wherein said R$^5$ is alkoxy.

26. A compound as defined in claim 21 wherein said R$^5$ is —NHCOCH$_3$.

27. A compound as defined in claim 21 wherein said R$^5$ is pyrrolidino.

28. A compound as defined in claim 21 wherein said R$^5$ is tetrahydro-2H,4H-1,3,6-dioxazocino.

29. A compound as defined in claim 12 wherein said R$^1$ and R$^2$ are methyl, R$^4$ is hydrogen, R$^5$ is —N,N—(dialkyl)-amino and R$^6$ and R$^7$ represent the carbon atoms necessary to complete a fused benzene ring.

30. A compound as defined in claim 12 wherein said R$^1$ and R$^2$ are methyl, R$^4$ and R$^6$ are hydrogen, R$^5$ is —N,N—(dialkyl)amino and R$^7$ is alkyl.

31. A compound as defined in claim 12 wherein said R$^1$ and R$^2$ are methyl, R$^4$, R$^5$ and R$^6$ are hydrogen and R$^7$ is hydroxy.

32. A compound as defined in claim 14 wherein said R$^1$ and R$^2$ are methoxy, R$^4$ and R$^6$ are hydrogen and R$^5$ and R$^7$ are alkoxy.

33. A compound as defined in claim 6 wherein said $R^1$, $R^2$, $R^3$, $R^4$, $R^5$, $R^6$ and $R^7$ are hydrogen.
34. The compound
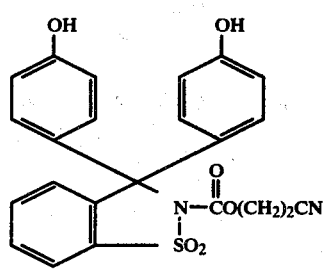
35. The compound
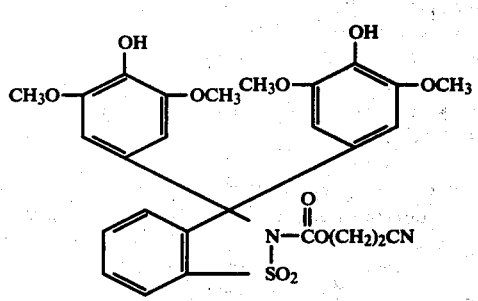
36. The compound
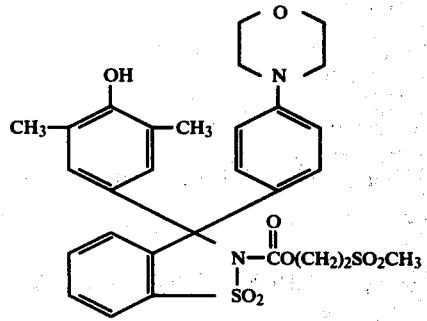
37. The compound
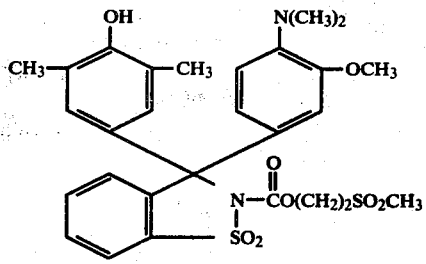
38. The compound
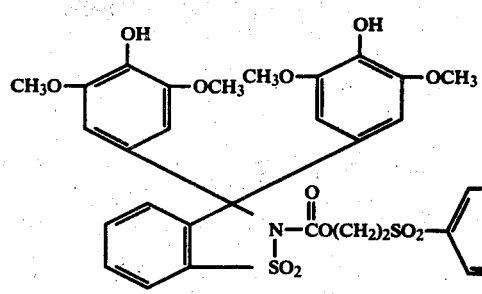
39. The compound
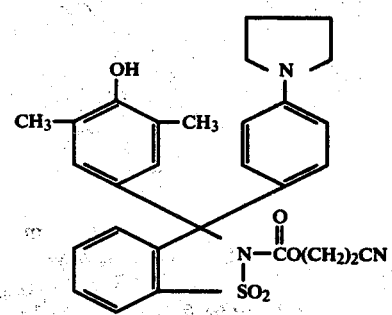
40. The compound
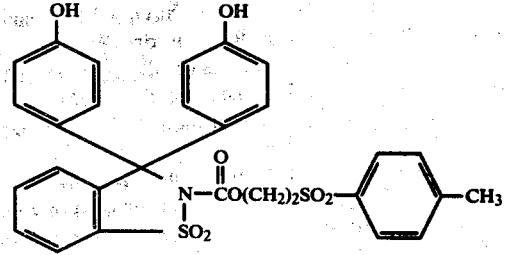
* * * * *